(12) United States Patent
Bastings et al.

(10) Patent No.: US 11,498,911 B2
(45) Date of Patent: Nov. 15, 2022

(54) PROCESS FOR PREPARING ETHYLENE CARBONATE AND ETHYLENE GLYCOL

(71) Applicant: SHELL OIL COMPANY, Houston, TX (US)

(72) Inventors: Roel Guillaume Hubertus Leonardus Bastings, Amsterdam (NL); Jesse Raymond Black, Houston, TX (US); Vesna Bojovic, Ras Laffan (QA); Wayne Errol Evans, Houston, TX (US); Gregory John Ward, Houston, TX (US)

(73) Assignee: SHELL USA, INC., Houston, TX (US)

( * ) Notice: Subject to any disclaimer, the term of this patent is extended or adjusted under 35 U.S.C. 154(b) by 240 days.

(21) Appl. No.: 16/769,553

(22) PCT Filed: Dec. 6, 2018

(86) PCT No.: PCT/EP2018/083748
§ 371 (c)(1),
(2) Date: Jun. 3, 2020

(87) PCT Pub. No.: WO2019/110713
PCT Pub. Date: Jun. 13, 2019

(65) Prior Publication Data
US 2021/0198227 A1    Jul. 1, 2021

(30) Foreign Application Priority Data
Dec. 8, 2017    (EP) ..................................... 17206137

(51) Int. Cl.
*C07C 29/50*    (2006.01)
*C07C 317/38*    (2006.01)
(Continued)

(52) U.S. Cl.
CPC ........... *C07D 317/38* (2013.01); *B01D 53/04* (2013.01); *B01D 53/70* (2013.01); *B01D 53/78* (2013.01);
(Continued)

(58) Field of Classification Search
CPC ................ B01D 53/78; B01D 2257/70; B01D 2253/1122; B01D 53/04; B01D 53/82;
(Continued)

(56) References Cited

U.S. PATENT DOCUMENTS 4,324,909 A * 4/1982 Horvitz ................... C07C 29/03
560/246
4,620,044 A * 10/1986 Chang ................... C07C 29/106
568/832
(Continued)

FOREIGN PATENT DOCUMENTS

EP    0776890 A2    6/1997
GB    2 107 712 A  *  5/1983    ............. C07C 68/06
(Continued)

OTHER PUBLICATIONS

International Search Report and Written Opinion received for PCT Patent Application No. PCT/EP2018/083748, dated Feb. 11, 2019, 10 pages.
(Continued)

*Primary Examiner* — Timothy C Vanoy
(74) *Attorney, Agent, or Firm* — Shell Usa, Inc.

(57) ABSTRACT

A process for producing ethylene glycol and/or ethylene carbonate, said process comprising contacting at least a portion of a recycle gas stream comprising an alkyl iodide impurity with a guard bed system positioned upstream of an ethylene oxide reactor to produce a treated recycle gas stream, wherein the guard bed system comprises silver on alumina; contacting an epoxidation feed stream comprising
(Continued)

an ethylene feed stream, oxygen, chloride moderator, and at least a portion of the treated recycle gas stream with an epoxidation catalyst in the ethylene oxide reactor to produce an epoxidation reaction product comprising ethylene oxide; and contacting at least a portion of the epoxidation reaction product comprising ethylene oxide with a liquid absorbent in the presence of an iodide-containing catalyst in an absorber to produce a product stream comprising ethylene carbonate and/or ethylene glycol and the recycle gas stream comprising the alkyl iodide impurity.

7 Claims, 1 Drawing Sheet

(51) Int. Cl.
  *B01J 21/04* (2006.01)
  *B01J 23/50* (2006.01)
  *B01D 53/04* (2006.01)
  *B01D 53/70* (2006.01)
  *B01D 53/78* (2006.01)
  *C07D 317/38* (2006.01)

(52) U.S. Cl.
  CPC ............... *B01J 21/04* (2013.01); *B01J 23/50* (2013.01); *C07C 29/50* (2013.01); *B01D 2253/1122* (2013.01); *B01D 2257/2068* (2013.01); *B01D 2257/70* (2013.01)

(58) Field of Classification Search
  CPC .. B01D 2257/2068; B01D 53/70; B01J 21/04; B01J 23/50; C07C 29/50; C07C 317/38; C07C 29/106; C07C 31/202; Y02P 20/151; Y02P 20/52
  See application file for complete search history.

(56) References Cited

U.S. PATENT DOCUMENTS

| | | | |
|---|---|---|---|
| 6,717,001 B2 | 4/2004 | Evans et al. | |
| 9,096,564 B2 | 8/2015 | Van Ogtrop et al. | |
| 9,174,928 B2 | 11/2015 | Evans et al. | |
| 10,525,409 B2* | 1/2020 | Lemanski | ............... C07C 29/12 |
| 10,526,300 B2* | 1/2020 | Evans | ................... B01D 53/02 |
| 2009/0286998 A1 | 11/2009 | Evans et al. | |
| 2018/0370936 A1* | 12/2018 | Evans | ................. C07D 301/32 |
| 2020/0392101 A1* | 12/2020 | Bastings | ............... B01D 53/02 |

FOREIGN PATENT DOCUMENTS

| | | | | |
|---|---|---|---|---|
| GB | 2107712 A | 5/1983 | | |
| WO | 2008144402 A2 | 11/2008 | | |
| WO | 2009021830 A1 | 2/2009 | | |
| WO | 2009140318 A1 | 11/2009 | | |
| WO | WO 2016 046 100 A1 * | 3/2016 | ............... | B01D 3/22 |
| WO | 2017102694 A1 | 6/2017 | | |
| WO | 2017102698 A1 | 6/2017 | | |
| WO | 2017102701 A1 | 6/2017 | | |
| WO | 2017102706 A1 | 6/2017 | | |
| WO | 2018069445 A1 | 4/2018 | | |

OTHER PUBLICATIONS

Brunauer et al., "Adsorption of Gases in Multimolecular Layers", Journal of the American Chemical Society, vol. 60, Issue No. 2, Feb. 1938, pp. 309-319.

Office Action Received for Taiwan Application No. 107143809, dated Jun. 30, 2022, 7 Pages(2 Pages of English Translation and 5 Pages of Official Copy).

* cited by examiner

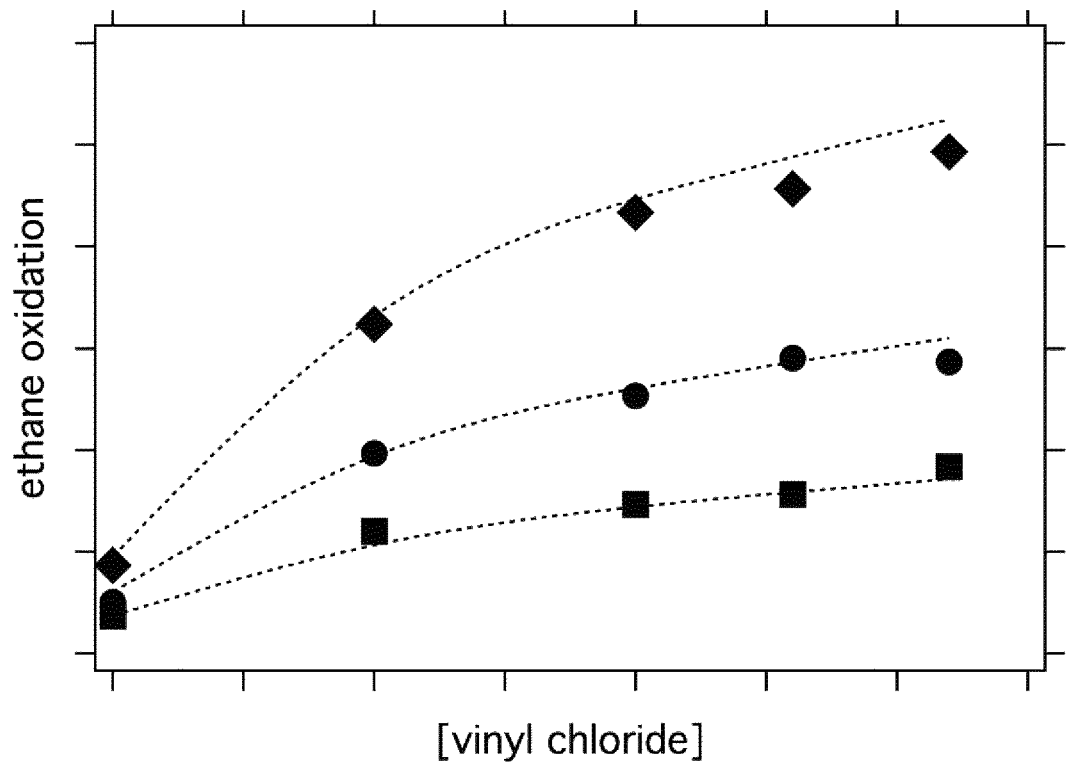

PROCESS FOR PREPARING ETHYLENE CARBONATE AND ETHYLENE GLYCOL

CROSS REFERENCE TO RELATED APPLICATIONS

This is a national stage application of International application No. PCT/EP2018/083748, filed 6 Dec. 2018, which claims priority of European application No. 17206137.6, filed 8 Dec. 2017.

FIELD OF THE INVENTION

The present invention relates to a process for the preparation of ethylene oxide, ethylene carbonate and/or ethylene glycol from ethylene, in particular a process wherein the formation of gaseous iodide impurities in a recycle gas stream is minimized.

BACKGROUND OF THE INVENTION

Ethylene glycol (EG) is a valuable industrial compound that is widely employed as starting material for the manufacture of polyester fibers and polyethylene terephthalate (PET) resins; it also finds application in automotive antifreeze and hydraulic brake fluids, aircraft de-icers as well as in pharmaceutical products.

Ethylene glycol is normally prepared from ethylene oxide (EO). Ethylene oxide is prepared by silver-catalyzed oxidation of ethylene. More specifically, ethylene and oxygen are passed over a silver oxide catalyst, typically at pressures of 10-30 bar and temperatures of 200-300° C., producing a product stream comprising ethylene oxide, carbon dioxide, ethylene, oxygen, and water. In order to control performance of the silver oxide epoxidation catalyst, a moderator (or "promoter") compound such as methyl chloride, ethyl chloride, ethylene dichloride or vinyl chloride is generally added to the ethylene oxide reactor feed. Methane is generally added to the feed gas as ballast gas in order to reduce flammability of ethylene.

In one well-known process, the ethylene oxide thus produced is reacted with a large excess of water in a non-catalytic process, producing a glycol product stream comprising close to 90 wt % monoethylene glycol (MEG), the remainder being predominantly diethylene glycol (DEG), some triethylene glycol (TEG) and a small amount of higher homologues. In another well-known process, ethylene oxide is reacted with carbon dioxide in the presence of a catalyst to produce ethylene carbonate. The ethylene carbonate is subsequently hydrolyzed to provide ethylene glycol. Reaction via ethylene carbonate significantly improves the selectivity of ethylene oxide conversion to monoethylene glycol.

In the last few decades, many efforts have been directed towards the development of simplified processes and equipment for producing alkylene glycols from alkylenes, notably ethylene glycol from ethylene. For example, GB2107712 describes a process for preparing monoethylene glycol wherein the gases from the ethylene oxide (EO) reactor are supplied directly to a reactor wherein ethylene oxide is converted to ethylene carbonate or to a mixture of ethylene glycol and ethylene carbonate.

EP 0776890 describes a process wherein the gases from the ethylene oxide reactor are supplied to an ethylene oxide absorber, wherein the absorbing solution mainly contains ethylene carbonate (EC) and ethylene glycol (EG). The ethylene oxide in the absorbing solution is supplied to a carboxylation reactor and allowed to react with carbon dioxide in the presence of a carboxylation catalyst. The ethylene carbonate in the absorbing solution is subsequently supplied, with the addition of water, to a hydrolysis reactor and subjected to hydrolysis in the presence of a hydrolysis catalyst.

EP2178815 describes a reactive absorption process for preparing monoethylene glycol, wherein the gases from the ethylene oxide reactor are supplied to a reactive absorber and the ethylene oxide is contacted with an aqueous lean absorbent in the presence of one or more carboxylation and hydrolysis catalysts, and wherein the majority of the ethylene oxide is converted to ethylene carbonate (EC) or ethylene glycol (EG) in the absorber.

In each of these cases, a gas stream containing gases that are not absorbed by the recirculating absorbent stream will be produced from the absorber. This gas stream is treated in a carbon dioxide absorption column and then recombined with any gases bypassing the carbon dioxide absorption column. The combined gases are then at least partially recycled, as recycle gas stream, to the EO reactor.

However, it has been found that in those processes where the carboxylation reaction is performed in a reactive absorber using an iodide-containing carboxylation catalyst, decomposition materials and side products may be present in the recycle gas stream and/or in the fat absorbent stream. Examples of such decomposition materials and side products include gaseous iodide-containing impurities, such as alkyl iodides (e.g., methyl iodide, ethyl iodide, etc.) and vinyl iodide.

The silver-based catalysts commonly employed in the conversion (epoxidation) of ethylene to ethylene oxide are very susceptible to catalyst poisoning, in particular poisoning by gaseous iodide-containing impurities, such as alkyl iodides and vinyl iodide. Catalyst poisoning impacts the epoxidation catalyst performance, in particular the selectivity and/or the activity, and shortens the length of time the epoxidation catalyst can remain in the epoxidation reactor before it becomes necessary to exchange the catalyst with fresh catalyst.

Accordingly, it is desirable to remove such catalyst poisons as much as is practicable from the recycle gas stream before it comes into contact with the epoxidation catalyst. To this end, various so-called "guard bed systems" positioned upstream of the EO reactor, as previously disclosed in, among others, EP2285795, EP2279182 and EP2155375 have been developed. Such guard bed systems typically comprise one or more vessels, each guard bed vessel comprising an inlet, an outlet, and a packed bed ("guard bed") comprising a solid absorbent ("guard bed material") capable of reducing the quantity of iodide-containing impurities in a fluid stream by chemical or physical means including, but not limited to, reaction with the impurities and absorption/adsorption of the impurities.

However, while such guard bed systems are highly efficient in removing substantial amounts of various types of impurities from the recycle gas stream upstream of the epoxidation catalyst, these guard beds gradually lose their capacity after extended exposure to impurities in the recycle gas stream. It is therefore highly desirable to minimize the formation of iodide compounds in the recycle gas stream throughout the process.

Alkyl iodides are formed in the ethylene oxide absorber by a halogen exchange $S_N2$ reaction with the iodide-containing carboxylation catalyst called the Finkelstein reaction:

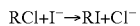

The higher the organic chloride levels in the ethylene oxide reactor product gas, the higher the formation of organic iodides in the ethylene oxide absorber will be. Vinyl chloride moderator does not directly participate in this reaction.

Generally, the promoting action of chloride moderators is achieved by donating their chlorine atom to the catalyst surface. This is a dynamic process, as ethylene, ethane, and methane (as ballast gas) present in the ethylene epoxidation feed gas continually strip chlorine from the catalyst surface, thus reforming vinyl chloride as well as forming ethyl chloride and methyl chloride, all of which can re-donate chlorine atoms to the surface. Ethylene oxide (EO) formed in the epoxidation reactor can also strip chlorine from the surface, forming more complex oxygenated organic chloride compounds, which do not appear to re-donate chlorine after they are formed. Overall, in this dynamic environment, a portion of vinyl chloride moderator added to the reactor is converted to ethyl chloride, methyl chloride, and oxygenated organic chlorides, i.e., more vinyl chloride is supplied to the reactor than it leaves.

It is known that ethylene and methane have a relatively low chlorine stripping power. Conversely, ethane has a high stripping power, and the amount of ethane in the recycle gas stream can strongly fluctuate as it is a common impurity in the ethylene feed. Such fluctuations may occur due to an inadequate control of ethane levels by the ethylene feed gas supplier, due to aging of the epoxidation catalyst, requiring more ethylene to be fed to maintain production, or a combination thereof. Ethane may also be present in the methane ballast feed, but generally contributes to no more than 5% of total ethane entering the process. Due to the large stripping power of ethane, increases in ethane levels in the ethylene feed gas (and recycle gas) result in direct and large increases in ethyl chloride (EC) levels. In addition, increased vinyl chloride moderator dosing (to maintain selectivity with catalyst aging) results in higher surface chloride levels, thus resulting in a direct increase in VC levels and an indirect increase in ethyl chloride (EC) and methyl chloride levels (MC) due to surface chlorine stripping.

As noted above, the ethane concentration in the recycle gas stream is dependent on the amount of ethane naturally present in the ethylene feed supplied to the ethylene oxide reactor. Ethane is typically partially removed from the recycle gas stream through an argon purge that is common to the ethylene epoxidation process. In addition, ethane may vanish from the recycle gas stream due to slow oxidation (combustion), catalyzed by surface chlorine, to carbon dioxide ($CO_2$) and water over the epoxidation catalyst. Ethylene and methane concentrations on the other hand are generally maintained at stable levels in the recycle gas during operation.

It is evident from the foregoing that the interdependence of ethane concentration, organic chloride levels and organic iodide formation is complex. On the one hand ethane is converted to ethyl chloride, and on the other hand surface chlorine (some of which comes from ethyl chloride) increases oxidation of ethane. It follows that as total chloride loop gas concentration is increased to compensate for catalyst aging, ethane oxidation increases; however, under these conditions, ethyl chloride levels (and therefore ethyl iodide levels) increase, too.

Considering that, as described above, ethyl iodide and methyl iodide are extremely poisonous for the epoxidation catalyst and their concentrations are dependent on the dynamic interplay of vinyl chloride, ethyl chloride, methyl chloride and ethane levels in the recycle gas stream both at standard operating conditions (SOC) and extended operating conditions (EOC), a need has arisen for a process for the preparation of ethylene oxide, ethylene carbonate and/or ethylene glycol from ethylene which addresses the foregoing issues.

Accordingly, the inventors have sought to provide an improved process for the preparation of ethylene oxide, ethylene carbonate and/or ethylene glycol from ethylene, in particular a process which minimizes the formation of iodide impurities to acceptable limits while achieving high ethylene conversion yields over the epoxidation catalyst life cycle.

SUMMARY OF THE INVENTION

Accordingly, there is provided a process for producing ethylene glycol and/or ethylene carbonate, said process comprising contacting at least a portion of a recycle gas stream comprising an alkyl iodide impurity with a guard bed system positioned upstream of an ethylene oxide reactor to produce a treated recycle gas stream, wherein said guard bed system comprises a guard bed material comprising silver on alumina;

contacting an epoxidation feed stream comprising an ethylene feed stream, oxygen, chloride moderator, and at least a portion of the treated recycle gas stream with an epoxidation catalyst in the ethylene oxide reactor to produce an epoxidation reaction product comprising ethylene oxide; and contacting at least a portion of the epoxidation reaction product comprising ethylene oxide with an absorbent in the presence of an iodide-containing catalyst in an absorber to produce a product stream comprising ethylene carbonate and/or ethylene glycol and the recycle gas stream comprising the alkyl iodide impurity, wherein the epoxidation feed stream comprising ethylene feed stream, oxygen, moderator compound, and treated recycle gas stream contacted with the epoxidation catalyst in the ethylene oxide reactor comprises no more than 8000 ppmv of ethane, and wherein a vinyl chloride moderator is added to the epoxidation feed stream, wherein the concentration of vinyl chloride moderator added to the epoxidation feed stream is controlled such that the I-factor representing the relative quantity of chloride moderator species present in the epoxidation feed stream, defined as $$\text{I factor} = ([\text{vinyl chloride}] + [\text{ethyl chloride}] + [\text{methyl chloride}]/3) / ([\text{ethylene}] + 70 \cdot [\text{ethane}])$$

is in the range of 0.02-0.4.

BRIEF DESCRIPTION OF THE DRAWINGS

FIG. 1 shows the results of micro-reactor experiments of silver- and chloride-catalyzed ethane combustion.

DETAILED DESCRIPTION OF THE INVENTION

The present invention provides a process for producing ethylene glycol and/or ethylene carbonate from ethylene, wherein the formation of alkyl iodide impurities in the recycle gas stream is minimized.

The process of producing ethylene glycol and/or ethylene carbonate by epoxidation of ethylene and reactive absorption of ethylene oxide has been described in detail in, among others, WO2009021830, WO2009140318, WO2009140319, their disclosure incorporated herein by reference. Specifically, guard bed systems for use in this process have been described in detail in WO2008144402, WO2017102694, WO2017102698, WO2017102701 and WO2017102706.

Typically, this process comprises reacting, in an ethylene oxide reactor, ethylene with oxygen in the presence of an epoxidation catalyst to form ethylene oxide. In such a reaction, the oxygen may be supplied as oxygen or as air, but is preferably supplied as oxygen. Ballast gas, for example methane or nitrogen, is typically supplied to allow operation at high oxygen levels without causing a flammable mixture.

In accordance with the present invention, a vinyl chloride moderator compound is supplied for ethylene oxide catalyst performance control. Vinyl chloride is preferred over other chloride moderators, as it will not directly lead to raised methyl chloride and ethyl chloride levels in the epoxidation reactor feed, and concomitant increased formation of methyl iodide and ethyl iodide catalyst poisons.

The alkene, oxygen, ballast gas and moderator are preferably supplied to recycle gas that is supplied to the ethylene oxide reactor from an ethylene oxide absorber (preferably via a carbon dioxide absorption column). The catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the ethylene oxide reactor is preferably cooled in one or more coolers, preferably with generation of steam at one or more temperature levels.

The gas composition is then passed to a reactive absorber in which it is intimately contacted with "lean" absorbent. Typically, the lean absorbent comprises at least 20 wt % water. Preferably, the lean absorbent also comprises ethylene carbonate and/or ethylene glycol. At least a portion of, and preferably substantially all of the ethylene oxide in the gas composition is absorbed into the lean absorbent. In accordance with the present invention, the gas composition is intimately contacted with the lean absorbent in the present of one of more catalysts that promote carboxylation and hydrolysis. Suitably, the absorber may be the sort of reactive absorber described in WO2009021830 or in WO2016046100. Preferred homogeneous catalysts that are known to promote carboxylation include alkali metal iodides such as potassium iodide and halogenated organic phosphonium or ammonium salts such as tributylmethylphosphonium iodide, tetrabutylphosphonium iodide, triphenylmethylphosphonium iodide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate.

Preferred homogeneous catalyst systems include a combination of potassium iodide and potassium carbonate, and a combination of potassium iodide and potassium molybdate. Heterogeneous catalysts that promote carboxylation include quaternary ammonium and quaternary phosphonium iodides immobilized on silica, quaternary ammonium and quaternary phosphonium iodides bound to insoluble polystyrene beads, and metal (e.g. zinc) iodides, immobilised on solid supports containing quaternary ammonium or quaternary phosphonium groups, such as ion exchange resins containing quaternary ammonium or quaternary phosphonium groups.

Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

A "fat" absorbent stream is withdrawn from the alkylene oxide absorber, preferably by withdrawing liquid from the bottom of the alkylene oxide absorber, i.e. below the vertically stacked trays or packing. The fat absorbent stream will contain alkylene carbonate and/or alkylene glycol and any remaining EO, if present, depending on the conditions, set-up and catalyst in the absorber.

Any gases that are not absorbed in the absorber, including any catalyst decomposition products or side products, are removed from the top of the absorber and are ultimately recycled to the epoxidation reactor. Preferably, at least a portion of the gas to be recycled to the epoxidation reactor will be supplied to a carbon dioxide absorption column, wherein carbon dioxide is at least partially absorbed, before the thus-treated gas is supplied to the epoxidation reactor.

The present inventors have found that in particular organic iodide-containing impurities, and more in particular vinyl iodide and alkyl iodides such as ethyl and methyl iodide, in the recycle gas need to be reduced to very low levels in order for the performance of the epoxidation catalyst to remain unaffected by their presence.

In particular, the amount of alkyl iodide present in a partially treated recycle gas stream is preferably no more than 6 ppbv, more preferably no more than 5 ppbv, even more preferably no more than 3 ppbv, even more preferably no more than 2 ppbv, and most preferably no more than 1 ppbv. Further, the amount of vinyl iodide present in a treated recycle gas stream is preferably no more than 20 ppbv, preferably no more than 15 ppbv, preferably no more than 10 ppbv, more preferably no more than 5 ppbv, even more preferably no more than 4 ppbv, even more preferably no more than 3 ppbv, and most preferably no more than 1 ppbv. Similarly, the total amount of alkyl iodide and vinyl iodide present in a treated recycle gas stream supplied to the epoxidation reactor is preferably no more than 26 ppbv, preferably no more than 20 ppbv, preferably no more than 16 ppbv, preferably no more than 13 ppbv, preferably no more than 10 ppbv, more preferably no more than 7 ppbv, even more preferably no more than 5 ppbv, most preferably no more than 2 ppbv.

Such very low levels of iodide impurities in the recycle gas stream from the EO absorber supplied to the ethylene oxide (EO) reactor are obtainable by the use of one or more guard bed system positioned upstream of the EO reactor. Within such a guard bed system, the recycle gas stream passes through one or more, preferably two or more guard bed vessels and is contacted with the guard bed material in each guard bed vessel, whereby impurities, typically one or more iodide impurities, are at least partially removed. Depending on the impurities content of the gaseous feed, impurities will be removed in the first guard bed vessel and, possibly, any further guard bed vessel. A treated gaseous feed will be removed from the guard bed system. Said treated gaseous feed will have a reduced level of impurities.

As used herein, at least one of the guard bed materials is a silver on alumina-based support material. This type of guard bed material is particularly suited for removing alkyl iodide impurities, in particular methyl iodide and ethyl iodide, from the recycle gas stream. Suitably, the guard bed material capable of removing one or more alkyl iodide impurities from the recycle gas stream comprises an alumina support material, and deposited on the alumina support material, silver in an amount of from 2% to 10% by weight.

A small amount of potassium carbonate ($K_2CO_3$) is used to passivate the alumina and enhance the uptake of iodine. Preferably, the first support material comprises gamma-alumina. A suitable support material may have a surface area of more than 20 $m^2/g$, relative to the weight of the support material, or at least 25 $m^2/g$, or at least 50 $m^2/g$, or at least 75 $m^2/g$, or at least 100 $m^2/g$, or at least 125 $m^2/g$, or at most 1200 $m^2/g$, or at most 500 $m^2/g$, or at most 300 $m^2/g$, or at most 200 $m^2/g$, or at most 175 $m^2/g$, or from 20 $m^2/g$ to 1200 $m^2/g$, or from 50 $m^2/g$ to 500 $m^2/g$, or from 75 $m^2/g$ to 300 $m^2/g$, or from 100 $m^2/g$ to 200 $m^2/g$, or from 125 $m^2/g$ to 175 $m^2/g$, on the same basis. As used herein, "surface area" is understood to refer to the surface area of the support material as measured in accordance with the B.E.T. (Brunauer, Emmett and Teller) method as described in detail in Brunauer, S., Emmet, P. Y. and Teller, E., J. Am. Chem. Soc., 60, pgs. 309-316 (1938). Preferably, the alumina support material is a spherical support material and has a diameter of less than 2 mm, or 1.8 mm or less, or 1.6 mm or less, or 1.5 mm or less, or 1.3 mm or less, or 1.0 mm or less, or a diameter from 0.25 mm to less than 2 mm, or from 0.5 mm to less than 2 mm, or from 0.75 mm to less than 2 mm, or from 1 mm to less than 2 mm, or from 0.25 mm to 1.5 mm, or from 0.5 mm to 1.5 mm, or from 0.75 mm to 1.5 mm, or from 1 mm to 1.5 mm.

The one or more guard bed vessels comprising a silver on alumina-based guard bed material are preferably operated at a temperature of at least 100° C., more preferably at least 115° C., most preferably at least 120° C. In this embodiment, the one or more guard beds are preferably operated at a temperature of at most 145° C., more preferably at most 140° C., even more preferably at most 135° C., most preferably at most 130° C.

In some instances, the recycle gas stream passes through at least two guard bed systems, wherein a first guard bed systems is configured for removing one or more alkyl iodide impurities (such as methyl iodide and ethyl iodide) as described above to provide a partially treated recycle gas stream, wherein the partially treated recycle gas stream is subsequently provided to a second guard bed systems configured for removing one or more vinyl iodide impurities to provide a further treated recycle gas stream. Thus, in one embodiment, the recycle gas stream supplied to the guard bed system is further contacted with a second guard bed system comprising a guard bed material capable of removing at least a portion of a vinyl iodide impurity from the recycle gas stream, wherein the treated gaseous feed stream removed from the final guard bed vessel in series of the first guard bed system is supplied as the gaseous feed via a feed line to the second guard bed system.

A suitable guard bed material for removing vinyl iodide impurities from a recycle gas stream is a palladium/gold based material, preferably supported on silica. Thus, in one embodiment, the guard bed material capable of removing at least a portion of a vinyl iodide impurity comprises palladium and gold, preferably supported on silica. The use of such guard beds in a process for preparing ethylene carbonate and/or ethylene glycol has been described in detail in WO2017102701. In this embodiment, the one or more guard bed vessels comprising a palladium/gold based material are preferably operated at a temperature of at least 65° C., more preferably at least 70° C., most preferably at least 83° C. In this embodiment, the one or more guard bed vessels are preferably operated at a temperature of at most 95° C., more preferably at most 90° C., even more preferably at most 87° C., most preferably at most 85° C.

Preferably, the gaseous feed to be treated is recycle gas from a reactive absorber that has yet to be treated in a carbon dioxide absorption column. Positioning the guard bed system at this stage in the process may have the added advantage of protecting the $CO_2$ absorber from any potential effects that may be caused by the impurities that are removed by the guard bed system.

The feed line, optionally, contains one or more heating or cooling devices, such as heat exchangers, in order to alter the temperature of the gaseous feed to be optimal for the guard bed system.

Each bed of guard bed material may be contained within the guard bed vessel in any suitable system. Preferred systems include an axial fixed bed, wherein the gas to be treated is contacted with the bed of guard bed material as an axial flow, and a radial fixed bed, wherein the gas to be treated is supplied from the inlet to the outside of the fixed bed and passes through the fixed bed to the centre of the guard bed vessel and then to the outlet. A radial fixed bed is preferred, as such a bed generally will have a lower pressure drop.

In a preferred embodiment, two or more guard bed systems arranged in series are used, each guard bed system comprising one or more guard bed vessels arranged in sequential order. Herein, each guard bed vessel comprises an inlet, a bed of guard bed material and an outlet, wherein the inlet of each guard bed vessel is attached by means of valves to both the feed line and the outlet of the guard bed vessel preceding it in sequential order, wherein the outlet of each guard bed vessel is attached by means of valves to both the effluent line and to the inlet of the guard bed vessel following it in sequential order and wherein the guard bed vessel following the last guard bed vessel in sequential order is the first guard bed vessel in sequential order. In operation, once the amount of impurities in the gaseous feed leaving the first guard bed vessel in series approaches a pre-determined undesired level, the guard bed vessel is removed from the flow of the gaseous feed by operation of valves. The flow of the gaseous feed continues through the second guard bed vessel and any subsequent guard bed vessels. The guard bed material in the first guard bed vessel is then refreshed. Once the guard bed material in the first guard bed vessel is refreshed, flow of the gaseous feed through said guard bed vessel is restored by operation of valves. However, it is restored such that the first guard bed vessel is now the last guard bed vessel in series to be contacted with the gaseous feed. After a further period of time, again determined by monitoring of the level of impurities in the gaseous flow, the same steps are applied to the second guard bed vessel in series (which at this stage is contacted with the gaseous feed first), and so on. Guard bed systems of this type are described in detail in WO2017102694. A particular advantage of operating the one or more guard bed systems in this rotating way is that a very high proportion of catalyst poison impurities present in the recycle gas are removed, while at the same time, the guard bed system is used in a reliable, efficient and economic manner.

In any embodiment, the pressure in each guard bed system will be determined by the pressure of the gas loop in the overall system. A preferable operating pressure is in the range of from 1 to 4 MPa (gauge). A more preferable operating pressure is in the range of from 2 to 3 MPa (gauge).

In the process as described herein, a vinyl chloride moderator compound is continuously added to the epoxidation feed stream in order to control performance of the silver oxide epoxidation catalyst. The moderating action of chloride moderators is achieved by donating their chlorine atom to the catalyst surface. This is a dynamic process, as ethylene, ethane, and methane (as ballast gas) present in the ethylene epoxidation feed gas continually strip chlorine from the catalyst surface, thus reforming vinyl chloride as well as forming ethyl chloride (EC) and methyl chloride (MC) moderator compounds, all of which can re-donate chlorine atoms to the surface. Typically, the operation of an ethylene oxide process involves adjusting the moderator level to maintain optimum catalyst selectivity throughout the catalyst lifecycle.

In the process of the present invention, the amount of vinyl chloride moderator [VC] dosed to the epoxidation feed stream is adjusted by controlling the so-called I factor, which defines the relative quantities of chloride moderator species present in the epoxidation feed stream according to the following equation $$\text{I-factor}=([VC]+[EC]+[MC]/3)/([\text{ethylene}]+70*[\text{ethane}])$$

Herein, [VC], [EC], [MC] are the total concentrations of vinyl chloride, ethyl chloride and methyl chloride moderator, respectively, in ppmv, present in the epoxidation feed stream; [ethylene] and [ethane] are the total concentrations in vol % of ethylene and ethane, respectively, present in the epoxidation feed stream.

The present inventors have developed a comprehensive chloride promoter redistribution kinetic model, which takes into account formation and redistribution of the concentrations of vinyl chloride (VC), ethyl chloride (EC), and methyl chloride (MC) as they enter in the epoxidation feed stream and pass through the EO reactor. These redistribution reactions are assumed to occur through adsorption onto the epoxidation catalyst surface S forming a surface chloride species S—Cl and then stripping of said surface chloride species S—Cl by reaction with ethylene, ethane, methane, and ethylene oxide in the gas. This chloride moderator redistribution model further accounts for irreversible conversion of a portion of vinyl chloride moderator with ethylene oxide produced in the epoxidation reactor to oxygenated organic chlorides.

Previously, ethane has been considered to be a non-reactive component in the gas fed to an EO reactor. However, it was found by the inventors that ethane combusts over the epoxidation catalyst, thus reducing ethane concentration in the recycle gas. It was further found that the ethane combustion rate increases with surface chloride concentration on the epoxidation catalyst, and is therefore dependent on the (redistributed) concentrations of vinyl chloride (VC), ethyl chloride (EC), and methyl chloride (MC) present in the epoxidation feed stream.

Based on modeling of microreactor and pilot plant data with the above chloride redistribution and ethane combustion models, in combination with commercial plant operating data for epoxidation catalyst aging (which is affected by chloride levels and affects ethane combustion), the inventors have been able to model ethylene oxide reactor inlet concentrations of vinyl chloride, ethyl chloride and methyl chloride to ethane concentration and vinyl chloride moderator feed rate in the feed stream, throughout the catalyst lifecycle. Combined with pilot-plant modeling data for the conversion, through reaction with the iodide-containing carboxylation catalyst in the reactive absorber, of methyl chloride and ethyl chloride to methyl iodide and ethyl iodide, respectively, for the first time the inventors have been able to make accurate quantitative predictions of the formation of unwanted alkyl iodides in the recycle gas stream at any time in the epoxidation catalyst lifecycle. Such quantitative predictions are of utmost significance for the design of guard bed systems equipped to protect the epoxidation catalyst from poisoning with alkyl iodides, as too high levels of alkyl iodide impurities in the recycle gas stream provided to the guard beds necessitates unacceptably large guard bed adsorbent volumes and/or high exchange rates.

Accordingly, it has been found that the formation of organic iodides, notably methyl iodide and ethyl iodide, in the recycle gas stream of a process for the formation of ethylene carbonate and/or ethylene oxide can be limited to preferred levels, if the concentration of ethane in the epoxidation feed stream does not exceed 8000 ppmv, based on the epoxidation feed stream. In the present invention, said epoxidation feed stream may comprise ethane and the ethane amount in said epoxidation feed stream is at most 8000 ppmv. Preferably, the epoxidation feed stream comprises no more than 7000 ppmv of ethane, more preferably no more than 6000 ppmv of ethane, more preferably no more than 5000 ppmv of ethane, more preferably no more than 4000 ppmv of ethane, more preferably no more than 3000 ppmv of ethane, more preferably no more than 2000 ppmv of ethane, more preferably no more than 1500 ppmv of ethane.

As described above, the concentration of ethane in the epoxidation feed stream is at least partially determined by the concentration of ethane in the ethylene feed stream provided to the epoxidation reactor.

As used herein, "ethylene feed stream" refers to the stream of ethylene freshly supplied to the epoxidation reactor, i.e. not including ethylene present in the recycle gas stream which is also provided at the inlet of the epoxidation reactor. The term "epoxidation feed gas stream" refers to the total feed provided at the inlet of the epoxidation reactor, including (at least a portion of) the recycle gas stream removed from the top of the absorber (and preferably treated in a carbon dioxide absorption column), oxygen feed, ethylene feed and vinyl chloride moderator.

In the present invention, the ethylene feed stream may comprise ethane and the ethane amount in the ethylene feed stream may be at most 1200 ppmv. Preferably, the ethylene feed stream comprises no more than 1200 ppmv of ethane, more preferably no more than 1000 ppmv of ethane, more preferably no more than 800 ppmv of ethane, even more preferably no more than 500 ppmv of ethane, yet even more preferably no more than 400 ppmv of ethane, yet even more preferably no more than 300 ppmv of ethane, most preferably no more than 200 ppmv of ethane, based on ethylene in the feed gas stream.

The amount of ethane in the ethylene feed stream can be limited by several methods known to the person skilled in the art, including (thermal) cracking, membrane separation, cryogenic distillation, or a combination thereof. In one embodiment, cryogenic distillation using a pressurized (typically in the order of 20 bar) column having at least 120 stages is employed, in which separation can further be improved by increasing the reflux.

In further accordance with the present invention, the feed rate of vinyl chloride moderator supplied to this feed stream is controlled such that throughout the process the I-factor, defining the relative concentrations of all (i.e., methyl chloride, ethyl chloride and vinyl chloride) chloride moderator species, as defined above is maintained within the range of 0.02-0.40. It has been observed in the modeling studies presented herein that maintaining a narrower I-factor range further limits the formation of methyl iodide and ethyl iodide contaminants in the recycle gas stream. Accordingly, preferably, throughout the entire epoxidation catalyst lifecycle the I-factor is maintained in the range of 0.02-0.2, more preferably in the range of 0.05-0.16, most preferably in the range of 0.08-0.16.

Typically, in accordance with the present invention, vinyl chloride moderator is dosed to the reactor feed such that vinyl chloride moderator is present in the epoxidation feed stream in a concentration of 0.5-20 ppmv, preferably in a concentration of 1-10 ppmv, more preferably 2-8 ppmv based on the epoxidation feed stream.

An advantage of the process of the present invention is that by controlling both the levels of ethane in the epoxidation feed gas and the relative quantity of chloride moderator species (expressed as I-factor) as defined herein, wherein vinyl chloride moderator is added to the epoxidation feed stream, the concentration of alkyl iodides in the recycle gas stream provided to a guard bed system upstream of the epoxidation reactor is minimized, whilst satisfactory ethylene oxide production parameters are maintained. This obviates the need of installing unacceptably large guard bed adsorbent volumes and/or uneconomically high guard bed exchange rates. In the present invention, the recycle gas stream contacted with the guard bed system may comprise methyl iodide and ethyl iodide and the total amount of methyl iodide and ethyl iodide in said recycle gas stream may be at most 1600 ppbv. In accordance with the present invention, preferably the total concentration of methyl iodide and ethyl iodide in the recycle gas stream contacted with the guard bed system does not exceed 1600 ppbv, more preferably does not exceed 1200 ppbv, more preferably does not exceed 800 ppbv, even more preferably does not exceed 600 ppbv, most preferably does not exceed 400 ppbv, based on the recycle gas stream.

The concentrations of organic chlorides, organic iodides and ethane in the recycle gas stream and epoxidation feeds stream can be determined by online and offline analyzers known in the art, such as gas chromatography (GC) and Gas Chromatography-Mass Spectrometry (GC-MS) apparatuses, for example an online analyzer described in co-pending application PCT/EP2017/076069.

Another benefit of the present invention is that controlling ethane levels and organic chloride levels in the reactor feed stream leads to reduced formation of inorganic chloride contaminants, which may result from reaction of organic chlorides with the, e.g. potassium-containing, carboxylation and/or hydrolysis catalyst. Typically, such inorganic chloride contaminants are removed with the catalyst bleed. However, as the customary recovery of the catalyst from this bleed is expensive, the quantity of catalyst bleed should be limited as much as possible. By controlling ethane levels and organic chloride levels in the reactor feed stream, less organic chlorides are formed, and consequently less inorganic chloride contaminants, thus allowing a smaller catalyst bleed if such bleed is determined by maximum allowable chloride concentration.

The invention is further illustrated by the following Example.

EXAMPLE

A proprietary ethane oxidation/chloride moderator redistribution kinetic model was developed. This model includes mass balances and reaction equations for silver- and chloride-catalyzed ethane combustion as a function of temperature, oxygen concentration, and chloride moderator concentration. The model further includes algorithms for redistribution of chloride concentration through adsorption of dosed vinyl chloride moderator on the epoxidation catalyst surface and desorption ("stripping") by ethylene, ethane and methane to form vinyl chloride (VC), ethyl chloride (EC) and methyl chloride (MC), as well as irreversible formation of oxygenated organic chlorides through reaction of adsorbed chloride with ethylene oxide.

FIG. 1 shows the results of micro-reactor experiments of silver- and chloride-catalyzed ethane combustion (8 vol % oxygen) over a high-selectivity silver-based epoxidation catalyst (CRI) using vinyl chloride as moderator, as a function of vinyl chloride moderator concentration and at different reaction temperatures, i.e. 260° C. (diamonds), 245° C. (circles) and 230° C. (squares). Also shown, as solid lines, are best fits to the experimental micro-reactor data using the above-described kinetic model for chloride-catalyzed ethane combustion and chloride moderator redistribution. It can be seen that using the chloride moderator redistribution kinetic model, good to excellent fits of the experimentally observed chloride-catalyzed ethane combustion dependence on vinyl chloride moderator concentration in the feed are obtained.

Additionally, a catalyst aging function was determined from commercial plant operating data using the same high-selectivity silver-based epoxidation catalyst (CRI) and applying physical and reactive mass balancing modeling.

These combined models were used to model pilot plant and micro-reactor ethylene epoxidation data. The data fit was very good to excellent, providing rate constants and activation energies for the above-described rate equations. In addition, equilibrium rate constants for the formation of methyl iodide (MI) and ethyl iodide (EI) from methyl chloride (MC) and ethyl chloride (EC) in the presence of iodide-containing carboxylation catalyst in the reactive absorber were derived from modeling studies of pilot plant data.

The performance of a commercial plant for the production of ethylene carbonate and/or ethylene glycol from ethylene oxide was calculated using this full model, and including equations for the epoxidation of ethylene to ethylene oxide, and to carbon dioxide and water, using ethane concentration in the ethylene feed and I-factor range as parameters. The minor contribution of ethane in the methane ballast of the epoxidation feed stream to the total of ethane entering the process was not included in the calculations. However, the partial removal of ethane from the recycle gas stream through an argon purge (typically at most 5 vol % based on the epoxidation feed stream) that is common to a commercial ethylene epoxidation process was accounted for in the mass balance.

Calculations were made over the full catalyst life cycle, using known values for the optimal catalyst operating temperature and the cumulative ethylene oxide production during catalyst life cycle. These temperatures were used to determine the optimal I-factor range at any month in the cycle, while the production was used with the aging function to calculate catalyst activity for ethane oxidation (combustion).

Table 1 below shows the results of a typical calculation as described above, representing the concentrations of epoxidation reactor feed gas components in a commercial plant for the production of ethylene carbonate and/or ethylene glycol from ethylene oxide at 5 months into the process, at an I-factor of 0.0928, as a function of ethane concentration in the ethylene feed. Also shown are the calculated concentrations of methyl iodide and ethyl iodide in the recycle gas stream at the inlet of the first guard bed in line.

TABLE 1

| I-factor | Ethylene Feed Ethane ppmv | EO Reactor Feed | | | | Guard Bed Feed | |
|---|---|---|---|---|---|---|---|
| | | Ethane ppmv | VC ppmv | EC ppmv | MC ppmv | MI ppbv | EI ppbv |
| 0.0928 | 200 | 1323 | 3.65 | 0.44 | 0.062 | 126 | 136 |
| 0.0928 | 400 | 2609 | 4.04 | 0.88 | 0.063 | 129 | 262 |
| 0.0928 | 500 | 3243 | 4.22 | 1.11 | 0.064 | 131 | 347 |
| 0.0928 | 850 | 5426 | 4.84 | 1.91 | 0.065 | 134 | 599 |
| 0.0928 | 1200 | 7572 | 5.41 | 2.73 | 0.067 | 137 | 854 |
| 0.0928 | 1300 | 8180 | 5.57 | 2.97 | 0.067 | 137 | 928 |

It can be observed from these calculations that at constant I-factor, ethane concentration in the ethylene feed has a marked effect on the concentration of ethane in the epoxidation reactor feed, as well as on the formation of methyl chloride, ethyl chloride and vinyl chloride in the epoxidation reactor, the most dominant effect being observed for the formation of ethyl chloride. It can further be seen that the formation of ethyl chloride has a direct and marked effect on the formation of ethyl iodide in the recycle gas loop.

These data show that reducing ethane content in ethylene feed by 100 ppmv has a large beneficial effect of reducing total iodide production by ~100 ppbv. It was further observed that a narrower I-factor range will result in further reduction in iodides of ~40 ppbv.

That which is claimed is:

1. A process for producing ethylene glycol and/or ethylene carbonate, said process comprising:
    contacting at least a portion of a recycle gas stream comprising an alkyl iodide impurity with a guard bed system positioned upstream of an ethylene oxide reactor to produce a treated recycle gas stream, wherein said guard bed system comprises a guard bed material comprising silver on alumina;
    contacting an epoxidation feed stream comprising an ethylene feed stream, oxygen, chloride moderator, and at least a portion of the treated recycle gas stream with an epoxidation catalyst in the ethylene oxide reactor to produce an epoxidation reaction product comprising ethylene oxide; and
    contacting at least a portion of the epoxidation reaction product comprising ethylene oxide with a liquid absorbent in the presence of an iodide-containing catalyst in an absorber to produce a product stream comprising ethylene carbonate and/or ethylene glycol and the recycle gas stream comprising the alkyl iodide impurity,
    wherein the epoxidation feed stream comprising ethylene feed stream, oxygen, moderator compound, and treated recycle gas stream contacted with the epoxidation catalyst in the ethylene oxide reactor comprises no more than 8000 ppmv of ethane, and
    wherein a vinyl chloride moderator is added to the epoxidation feed stream,
    wherein the concentration of vinyl chloride moderator added to the epoxidation feed stream is controlled such that the I-factor representing the relative quantity of chloride moderator species present in the epoxidation feed stream, defined as I factor=([vinyl chloride]+[ethyl chloride]+[methyl chloride]/3)/([ethylene]+70*[ethane])

is in the range of 0.02-0.4.

2. The process according to claim 1, wherein the epoxidation feed stream comprising ethylene feed stream, oxygen, moderator compound, and treated recycle gas stream contacted with the epoxidation catalyst in the ethylene oxide reactor comprises no more than 7000 ppmv of ethane.

3. The process according to claim 1, wherein the ethylene feed stream comprises no more than 1200 ppmv of ethane, based on ethylene in the feed gas stream.

4. The process according to claim 1, wherein the I factor is in the range of 0.02-0.2.

5. The process according to claim 1, wherein the total concentration of methyl iodide and ethyl iodide in the recycle gas stream contacted with the guard bed system does not exceed 1600 ppbv, based on the recycle gas stream.

6. The process according to claim 1, wherein the recycle gas stream supplied to the guard bed system is further contacted with a second guard bed system comprising a guard bed material capable of removing at least a portion of a vinyl iodide impurity from the recycle gas stream,
    wherein the treated gaseous feed stream removed from the final guard bed vessel in series of the first guard bed system is supplied as the gaseous feed via a feed line to the second guard bed system.

7. The process according to claim 6, wherein the guard bed material contained within the second guard bed system arranged in series comprises palladium and gold.

* * * * *